(12) United States Patent
Luo et al.

(10) Patent No.: US 7,470,667 B2
(45) Date of Patent: Dec. 30, 2008

(54) METHODS OF TREATING CANCER USING A MODIFIED ENDOSTATIN PROTEIN

(75) Inventors: Yongzhang Luo, Beijing (CN); Zhuobing Zhang, Beijing (CN); Qingxin Lei, Beijing (CN); Yan Sun, Beijing (CN); Jinwan Wang, Beijing (CN)

(73) Assignee: Medgenn (Hong Kong) Ltd, FanLing New Territory, Hong Kong (CN)

( * ) Notice: Subject to any disclaimer, the term of this patent is extended or adjusted under 35 U.S.C. 154(b) by 0 days.

(21) Appl. No.: 11/118,109

(22) Filed: Apr. 29, 2005

(65) Prior Publication Data

US 2006/0058232 A1    Mar. 16, 2006

Related U.S. Application Data

(63) Continuation-in-part of application No. 10/313,638, filed on Dec. 5, 2002, now Pat. No. 7,078,485.

(51) Int. Cl.
*A61K 38/00*    (2006.01)

(52) U.S. Cl. ........................................................ 514/12
(58) Field of Classification Search ...................... 514/2, 514/12, 789
See application file for complete search history.

(56) References Cited

U.S. PATENT DOCUMENTS 6,825,167 B1 * 11/2004 Yokoyama et al. ............ 514/12
6,949,514 B2 *  9/2005 Wallner et al. ................ 514/14

FOREIGN PATENT DOCUMENTS

WO        00/26368    *  5/2000

\* cited by examiner

*Primary Examiner*—Maryam Monshipouri
(74) *Attorney, Agent, or Firm*—Heslin Rothenberg Farley & Mesiti P.C.

(57) ABSTRACT

The present invention provides methods of treating an angiogenesis-related disease of a subject using a therapeutically effective amount of a modified endostatin protein. In particular, the methods encompass treating an angiogenesis-related disease of a subject using a combination of the modified endostatin, and a known cancer therapy agent such as a chemotherapy agent, or a radiotherapy agent.

7 Claims, 6 Drawing Sheets

METHODS OF TREATING CANCER USING A MODIFIED ENDOSTATIN PROTEIN

CROSS REFERENCE TO RELATED APPLICATIONS

This application is a continuation-in-part application of U.S. patent application Ser. No. 10/313,638, filed Dec. 5, 2002 now U.S. Pat. No. 7,078,485, the entire content of which is incorporated herein by reference.

FIELD OF THE INVENTION

This invention generally relates to the therapeutic use of endostatin, in particular, a modified endostatin which has an additional metal chelating peptide sequence at its N Terminal. The invention further relates to the use of the modified endostatin in treating a cancer of a patient, in particular, treating a cancer of a patient in combination with one or more known cancer therapy.

BACKGROUND OF THE INVENTION

Angiogenesis, the process of new blood vessel development and formation, plays an important role in numerous physiological events, both normal and pathological. Angiogenesis occurs in response to specific signals and involves a complex process characterized by infiltration of the basal lamina by vascular endothelial cells in response to angiogenic growth signal(s), migration of the endothelial cells toward the source of the signal(s), and subsequent proliferation and formation of the capillary tube. Blood flow through the newly formed capillary is initiated after the endothelial cells come into contact and connect with a preexisting capillary.

Angiogenesis is indispensable for embryonic development, organogenesis, tissue regeneration and repair, wound healing and female reproductive processes (Folkman, J. And Shing, Y., J. Biol. Chem. 267:109931-10934, 1992; Folkman, J., Nature Medicine 1: 27-31, 1995). Meanwhile, angiogenesis is also one of the necessary factors that cause the progression and deterioration of many pathological disorders including cancer growth and metastasis, cardiovascular disease, diabetic retinopathy, rheumatoid arthritis, etc. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis.

Angiogenesis is a complex multi-stage process that includes proliferation, migration and differentiation of endothelial cells, proteolytic degradation of the basement membrane, differentiation and migration of endothelial cells into the surrounding stroma, and finally formation of vasculature and new capillaries. The naturally occurring balance between endogenous stimulators and inhibitors of angiogenesis is one in which inhibitory influences predominate (Rastinejad et al., 1989, Cell 56:345-355).

Angiogenesis stimulators that can be mentioned include vascular endothelial growth factor (VEGF), vascular permeability factor (VPF), fibroblast growth factor (FGF-1 and -2), etc. On the other hand, some angiogenesis inhibitors have also been found and identified, which includes a 29 kDa fragment of fibronectin, thrombospondin (TSP-1), platelet factor 4, a 16 kDa fragment of prolactin, and a 38 kDa fragment of plasminogen and the like. In particular, O'Reilly et al. identified and characterized an internal 38 kDa fragment of plasminogen as angiostatin and a 20 kDa globular C-terminal of collagen XVIII as endostatin. It is suggested based on the current research results that the angiogenesis phenotype in the tissue depends on the dynamic equilibrium of angiogenesis stimulator and inhibitors in the local tissue environment (Folkman, J., N. Engl. J. Med. 333: 1757-1763, 1995).

Particularly interesting is that recent research shows that most angiogenesis inhibitors as mentioned above display the inhibitory activity of endothelial cell proliferation only after their parent proteins are hydrolyzed and form terminal or internal fragments. Thus, it is suggested that protein hydrolysis by endogenous peptidases plays a key role in the expression of their biological activities (O'Reilly, M. S. et al., Cell 88:277-285, 1997).

As a 20 kDa carboxyl terminal fragment of collagen XVIII, endostatin is a special inhibitor of endothelial cell proliferation and migration, and it also markedly inhibits the growth of many kinds of cancers (O'Reilly, M. S. et al., Cell 88: 277-285, 1997; U.S. Pat. No. 5,854,205). It was shown that repeated endostatin administration leads to prolonged stable state of mice cancers, and there was no induction of drug resistance (Boehm, T. et al., Nature 390:404-407, 1997). It was further shown that endostatin causes cells to be quiescent at cell cycle G1 phase and specifically induces apoptosis of endothelial cells (Dhanabalk, M. et al., Biochem. Biophys. Res. Commun. 258: 345-352, 1999).

Endostatin was initially isolated from a hemangioendothelioma cell line for its ability to inhibit the proliferation of capillary endothelial cells (O'Reilly, M. S. et al., Cell 88:277-285, 1997). Based on the analysis of its nucleotide sequence, O'Reilly et al. further expressed endostatin protein in an *E. coli* expression system in un-refolded form, and it is believed that the unfolded purified protein facilitates its prolonged release at the subcutaneous injection site. The authors also mentioned that when endostatin was refolded by a standard method and soulblized into tissue culture media, it strongly inhibited the proliferation of endothelial cells. Unfortunately, about 99% of protein was lost during protein refolding. In addition, though it has been reported that protein having anti-angiogenesis activity can be expressed in prokaryotes, the product can hardly refold into soluble form and tends to precipitate out of the solution. Further, cloning and expressing soluble recombinant endostatin in a yeast (*Pichia pastoris*) system were also reported (see, for example, Dhanabal, M. Et al., Cancer Res. 59: 189-197, 1999).

It has been shown that the requisite effective amount of endostatin expressed in yeast system is astonishingly high, about 240-600 mg/m$^2$/person in recent clinical trials. It is reasonable to speculate that such a high dose of drug would place a great and burdensome demand on large scale manufacturing of the drug for clinical trials and on industrial production in the future sales and marketing of the drug made from endostatin, even though it appears the high dose might be safe as determined in mouse and monkeys. There have been efforts made in reducing the dosage of endostatin and increasing the effect of endostatin by using continuous infusion with pumps in clinical trials. However, this approach can cause great discomfort and inconvenience for the patients and it does not lead to an obviously improved clinical result.

In U.S. patent application Ser. No. 10/313,638, applicants disclosed a novel modified endostatin produced in *E. coli*, and more importantly, the *E. coli* produced endostatin has better in vivo stability and biological activity than native endostatin produced in yeast, thereby markedly improving its pharmaceutical activity and substantially decreasing the requisite clinical administration doses. These findings can be seen from our previous experimental results, and pharmacological and pharmacokinetics studies. Other studies have shown that the administration of endostatin to tumor-bearing mice leads to significant tumor regression, and no toxicity or drug resistance has been observed even after multiple treatment cycles (Boehm et al., 1997, Nature 390(6658): 404-407). The fact that endostatin targets genetically stable endothelial cells and inhibits a variety of solid tumors makes it a very attractive candidate for anticancer therapy (Fidler and Ellis, 1994, Cell 79(2): 185-8; Gastl et al., 1997, Oncology 54(3): 177-84; van Hinsbergh et al., 1999, Ann Oncol 10 Suppl 4:60-3). In addition, angiogenesis inhibitors have been shown to be more effective when combined with radiation and chemotherapeutic agents (Klement, 2000, J. Clin Invest, 105(8) R15-24. Browder, 2000, Cancer Res. 6-(7) 1878-86, Arap et al., 1998, Science 279 (5349): 377-80; Mauceri et al., 1998, Nature 394 (6690): 287-91).

However, there have been no reports demonstrating the clinical efficacy of endostatin, especially *E. coli* produced modified endostatin. Currently, treatments such as surgery, chemotherapy, or radiotherapy have only achieved limited in treating cancer in human and animals. The present invention attempts to address the issue of inadequate and insufficient clinical efficacy of existing cancer therapy, and discloses a new method of therapy which takes advantage of the therapeutic use of the modified endostatin in treating angiogenesis-related diseases, in particular, cancer.

SUMMARY OF THE INVENTION

The present invention relates to a novel method of treating a cancer of a subject, in particular, of a human, using a modified endostatin molecule. The modified endostatin can be produced efficiently and effectively, and is a strong and promising candidate in reducing tumor growth.

The present invention provides a method of treating an angiogenesis-related disease of a subject, comprising the step of administering to the subject having the angiogenesis-related disease a therapeutically effective amount of a modified endostatin protein. Preferably, the subject is a mammal, and more preferably, the subject is a human.

According to one embodiment of the invention, the angiogenesis-related disease is a cancer.

According to another embodiment of the invention, the modified endostatin is administered to the subject together with a pharmaceutically acceptable carrier.

The present invention further provides a method of treating an angiogenesis-related disease of a subject, comprising the step of administering a modified endostatin to the subject in a therapeutically effective amount, in addition to treating the subject with a known cancer therapy suitable for treating said angiogenesis-related disease. Preferably, the know therapy is a cancer therapy, and more preferably, the cancer therapy is either chemotherapy or radiotherapy.

According to one embodiment of the invention, the chemotherapy encompasses the vinorelbine and cisplatin therapy.

According to another embodiment of the invention, the chemotherapy encompasses the cisplatin and paclitaxel therapy.

According to one embodiment of the invention, the chemotherapy encompasses the cisplatin and gemcitabine therapy.

According to yet another embodiment of the invention, the chemotherapy encompasses the docetaxel and cisplatin therapy.

The present invention provides a method of treating a cancer of a patient using a modified endostatin, in combination with a radiotherapy agent, and preferably, such radiotherapy agent is X-ray, or gamma radiation.

The present invention provides a method of treating a cancer of a patient, comprising administering to said patient a modified endostatin and at least one cancer therapy agent. Preferably, the cancer therapy agent is either a chemotherapy agent or a radiotherapy agent.

According to one embodiment of the invention, the modified endostatin is administered before the administration of the cancer therapy agent.

According to another embodiment of the invention, the modified endostatin is administered after the administration of the cancer therapy agent.

According to yet one embodiment of the invention, the modified endostatin is administered simultaneously with the administration of the cancer therapy agent.

Preferably, the modified endostatin used in the present invention comprises the amino acid sequence of SEQ ID NO.: 1.

Preferably, the modified endostatin used in the present invention comprises the amino acid sequence of SEQ ID NO.: 2.

The present invention further provides that the modified endostatin can be administered to the subject using clinically acceptable means of injection, which comprises a means selected from the group consisting of: topical, transdermal, intraperitoneal, intracranial, intracerebroventricular, intracerebral, intravaginal, intrauterine, oral, rectal, parenteral, intravenous, intraspinal, subcutaneous, and intramuscular.

The present invention provides a kit for treating a cancer of a patient, comprising a modified endostatin. Preferably, the kit of the present invention further comprises a suitable cancer therapy agent. More preferably, the suitable cancer therapy agent is either a chemotherapy agent, or a radiotherapy agent.

The present invention further provides a pharmaceutical composition for treating a cancer of a patient, comprising a modified endostatin and a pharmaceutically acceptable carrier.

Figure 1:
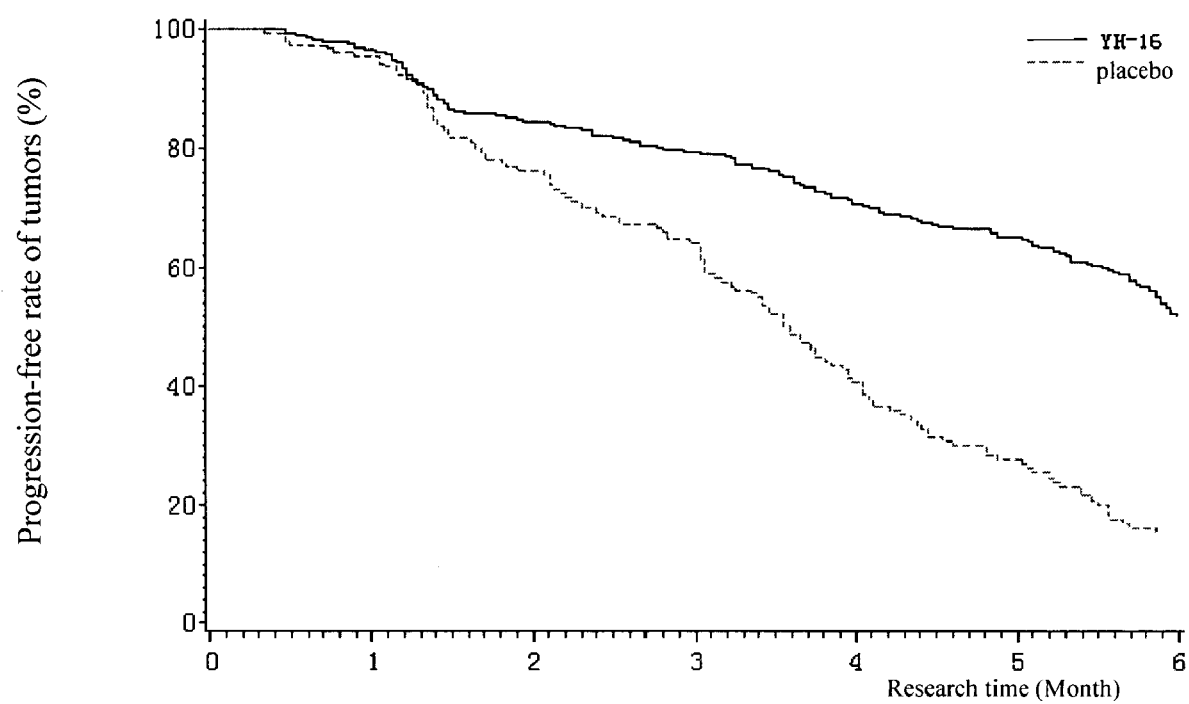
FIG. 1 shows a Kaplan-Meier analysis of tumor progression-free rate at each time point (ITT, Overall). In all Figures, dotted curve represents placebo, and solid curve represents YH-16 group.
Figure 2:
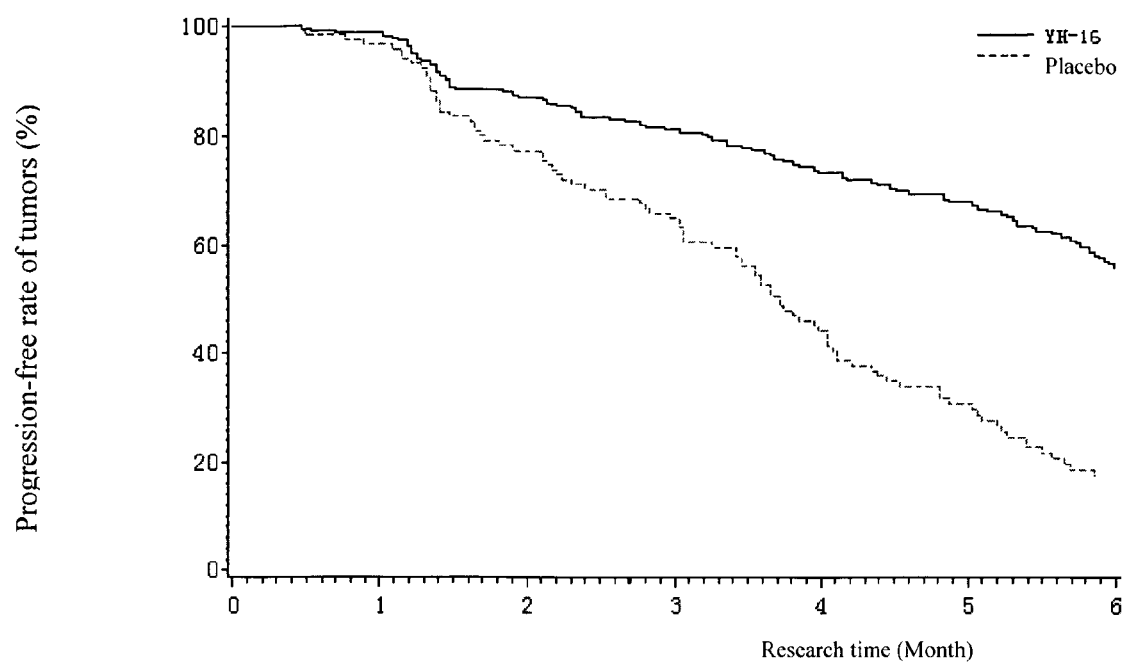
FIG. 2 shows a Kaplan-Meier analysis of tumor progression-free rate at each time point (ITT, initial treated group).
Figure 3:
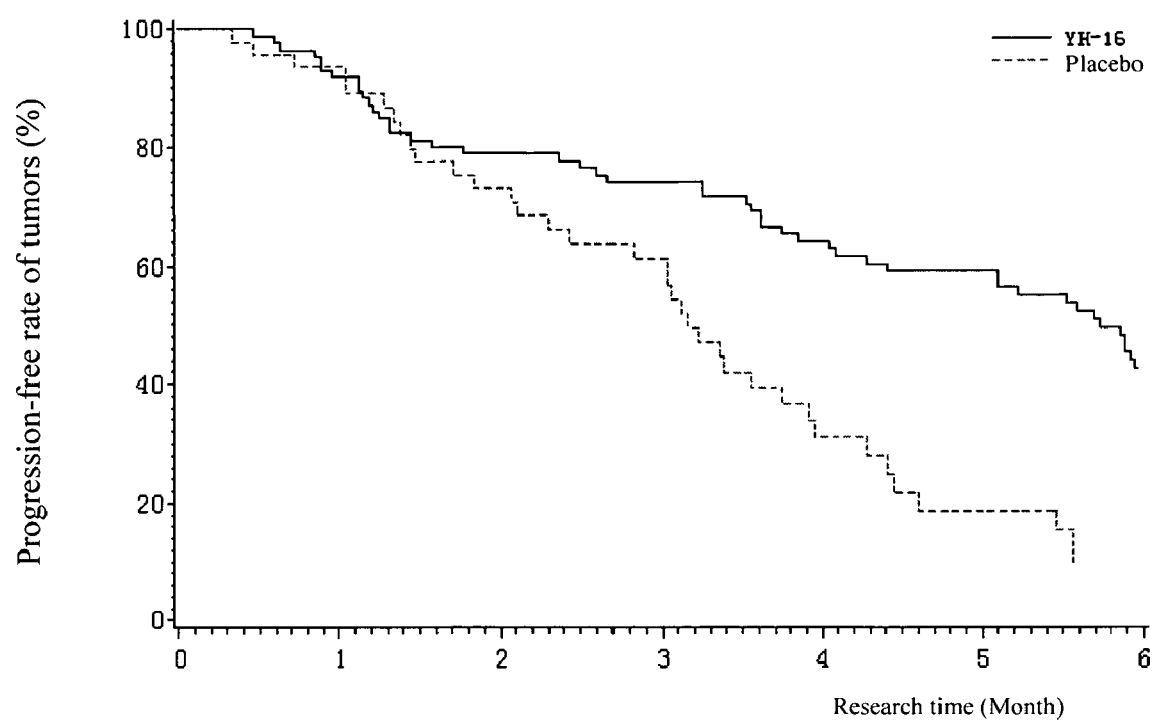
FIG. 3 shows a Kaplan-Meier analysis of tumor progression-free rate at each time point (ITT, re-treated group).

With respect to FIGS. 1-3, X-axes represent Study time (months), and Y-axes represent Tumor Progression-free Rate. The graphs show various Kaplan-Meier analyses of progression-free survival: 1) Overall patients; 2) initial treated group; 3) re-treated group. Here, the term "initial treated" group refers to those patients who are being treated with chemotherapy for the first time. The term "re-treated" group refers to patients who were treated with other forms of chemotherapy before undergoing treatment with the modified endostatin and NP. The term "Overall" group refers to data that are combined from the two groups. ITT stands for Intention-to-Treat.

Figure 4:
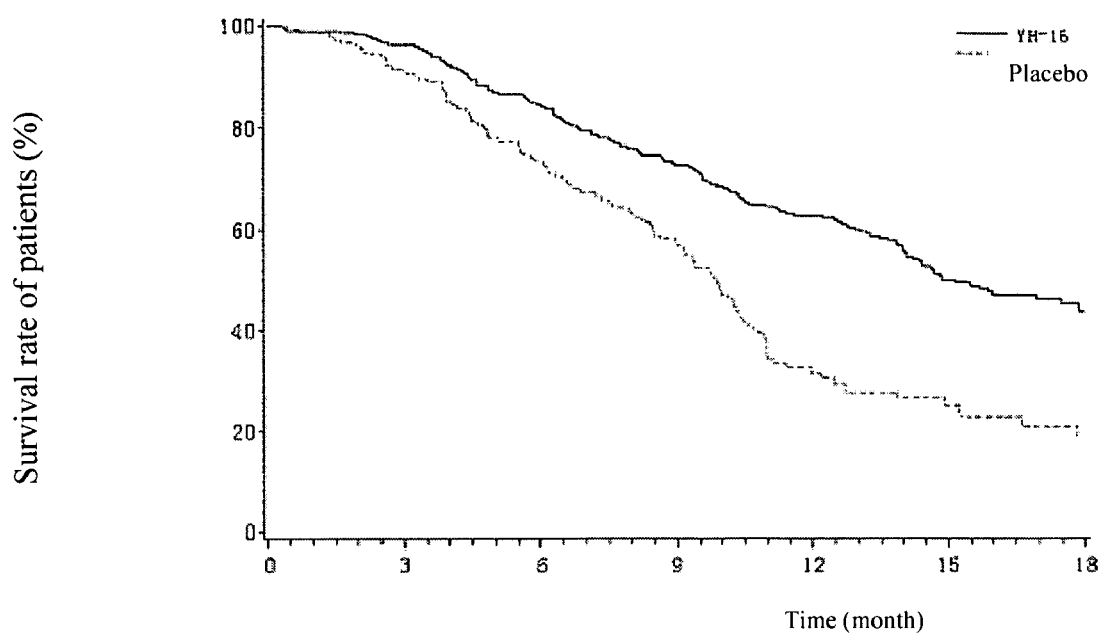
FIG. 4 shows a Kaplan-Meier survival estimate for patients treated with NP plus YH-16 and patients treated with NP plus placebo (Overall, ITT).
Figure 5:
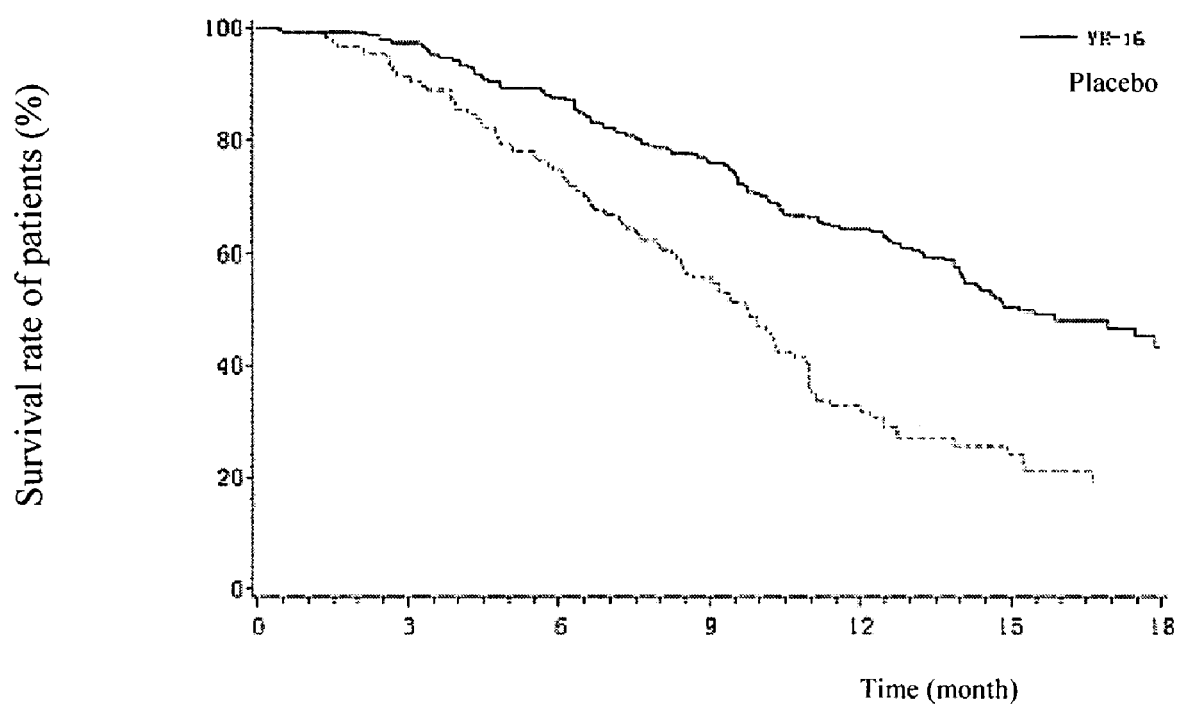
FIG. 5 shows a Kaplan-Meier survival estimate for patients treated with NP plus YH-16 and patients treated with NP plus placebo (initial treated group, ITT)
Figure 6:
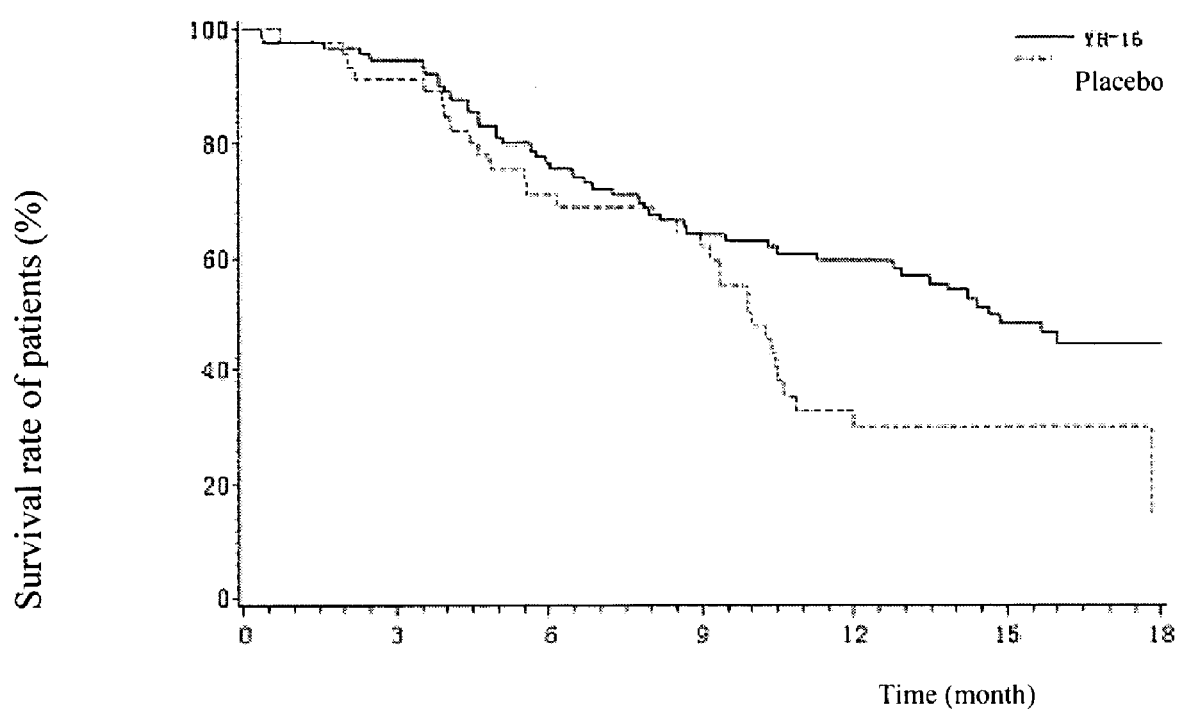
FIG. 6 shows a Kaplan-Meier survival estimate for patients treated with NP plus YH-16 and patients treated with NP plus placebo (re-treated group, ITT).

With respect to FIGS. 4-6, the graphs show Kaplan-Meier survival estimates for patients treated with NP plus YH-16 and patients treated with NP plus placebo. FIG. 4 corresponds to data from Overall patient; FIG. 5 corresponds to that of the initial treated group; and FIG. 6 corresponds to the re-treated group. In these three figures, X-axes represent "time" (months), and Y-axes represent "survival" (%).

DETAILED DESCRIPTION OF THE INVENTION

The present invention relates to the use of endostatin in treating angiogenesis-related diseases in a clinical setting, in particular the use of a modified endostatin in treating the cancer of a subject, especially a human.

The term "endostatin" as used herein refers to a protein that is preferably 18 kDa to 20 kDa in size as determined by non-reduced and reduced gel electrophoresis, respectively. The term endostatin also includes precursor forms of the 18 kDa to 20 kDa protein. The term endostatin also includes fragments of the 18 kDa to 20 kDa protein and modified proteins and peptides that have a substantially similar amino acid sequence, and which are capable inhibiting proliferation of endothelial cells. For example, silent substitutions of amino acids, wherein the replacement of an amino acid with a structurally or chemically similar amino acid does not significantly alter the structure, conformation or activity of the protein, is well known in the art. Such silent substitutions are intended to fall within the scope of the appended claims.

The term "endostatin" also includes shortened proteins or peptides wherein one or more amino acid is removed from either or both ends of endostatin, or from an internal region of the protein, yet the resulting molecule retains endothelial proliferation inhibiting activity. The term "endostatin" also includes lengthened proteins or peptides wherein one or more amino acid is added to either or both ends of endostatin, or to an internal location in the protein, yet the resulting molecule retains endothelial proliferation inhibiting activity.

The term "modified endostatin" refers to an endostatin molecule wherein its N terminal comprises at least 2-12 consecutive additional amino acids with metal binding properties. This term is also referred to as rh-Endostatin with additional amino acid sequence at the N terminal. An example of a modified endostatin comprises the following amino acid sequence:

```
MetGlyGlySerHisHisHisHisHis (SEQ ID NO.: 1)
```

The term "angiogenesis-related disease" refers herein to an abnormality or malfunctioning of a subject relating to the formation of blood vessels. Angiogenesis-related diseases include, but are not limited to angiogenesis-dependent cancer and other diseases of the body, including solid tumor, blood born tumors such as leukemias, and tumor metastases; benign tumors, such as hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; wound granulation; coronnary collaterals; cerebral collaterals; arteriovenous malformations; ischemic limb angiogenesis; diabetic neovascularization; macular degeneration; fractures; vasculogenesis; hematopoiesis; ovulation; menstruation; and placentation. In addition, angiogenesis-related diseases include, but are not limited to, intestinal adhesions, atherosclerosis, scleroderma, and hypertrophic scars, i.e., keloids. They also include diseases that have angiogenesis as a pathologic consequence such as cat scratch disease (*Rochele minalia quintosa*) and ulcers (*Helobacter pylori*).

The term "subject" as used herein refers to any mammalian subject including a human, an animal such as a dog, a cat, a rat, a rabbit, a monkey, or a mouse. Preferably, the subject refers to a human patient carrying cancer or tumor. The term "patient" herein refers to either a human or a mammal.

The term "cancer" as used herein refers to angiogenesis-dependent, abnormal growth of cells and tissues, and the growth requires an increase in the number and density of the blood vessels supplying them with blood. The term "cancer" is used interchangeably with the term "tumor" herein.

As used herein, the term "cancer therapy agent" refers to either a chemotherapy agent such as NP, or a radiotherapy agent such as X-ray or Gamma radiation.

As used herein, the term "known therapy" refers to any therapeutic treatment that is well accepted, and commonly used by the skilled artisan in treating a particular disease that the therapy is effective for.

The term "pharmaceutically acceptable" as used herein means that it is approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, olive oil, and the like. Saline is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic attenuated tumor-targeted bacteria, in purified form, together with a suitable amount of carrier so as to provide the form for proper administration to the patient. The formulation should suit the mode of administration.

The term "therapeutically effective amount" or "effective amount" as used herein refers to an amount of the modified endostatin is such as to produce the beneficial or desired effect in a subject which can be monitored using several end-points known to those skilled in the art. An effective amount can be administered in one or more administrations, applications or dosages.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin REMINGTON'S PHARM. SCI., 15th Ed. (Mack Publ. Co., Easton (1975)). The term "carrier" is used interchangeably herein with "excipient".

As used herein, the singular form "a," "an" and "the" include plural references unless the context clearly dictates otherwise. For example, the term "a subject" includes a plurality of subjects.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, a "composition" is intended to mean a combination of active agent, which in the present invention, refers to the modified endostatin, and another compound or composition, inert (for example, a detectable agent or label) or active, such as an adjuvant.

As used herein, a "pharmaceutical composition" is intended to include the combination of a modified endostatin with a carrier, inert or active, making the composition suitable for diagnostic or therapeutic use in vitro, in vivo, or ex vivo.

The present invention encompasses a method of treating an angiogenesis-related disease in a patient, whereby the patient is administered a modified endostatin. The modified endostatin which may be used in the methods of the invention can be produced in a variety of different ways, including synthetic (e.g., recombinant or chemically synthesized) modified endostatin, as well as naturally occurring endostatin with the requisite modification at its N terminal. The modified endostatin may have both naturally occurring and non-naturally occurring amino acid residues (e.g., D-amino acid residues) and/or one or more non-peptide bonds (e.g., imino, ester, hydrazide, semicarbazide, and azo bonds). The modified endostatin may also contain additional chemical groups (i.e., functional groups) present at the amino and/or carboxy termini, such that, for example, the stability, bioavailability, and/or inhibitory activity of the peptide is enhanced. Exemplary functional groups include hydrophobic groups (e.g. carbobenzoxyl, dansyl, and t-butyloxycarbonyl, groups), an acetyl group, a 9-fluorenylmethoxy-carbonyl group, and macromolecular carrier groups (e.g., lipid-fatty acid conjugates, polyethylene glycol, or carbohydrates) including peptide groups.

In a preferred embodiment, the modified endostatin contains at its N terminal the amino acid sequence of SEQ ID NO.: 1.

In another preferred embodiment, the modified endostatin contains at its N terminal the following amino acid sequence:

MetGlyGlySerHisHisHisHisHisHisSerHisArgAspPhe. (SEQ ID NO.: 2)

The subjects encompassed in the present invention include a human, an animal such as a dog, cat, pig, rabbit, mouse, rat, etc. Preferably, the present invention can be used in treating a human patient suffering from a cancer, in particular, a solid cancer.

In certain embodiments, the modified endostatin are used in conjunction with other known cancer therapies to treat a cancer of a subject, in particular, a human. For example, the modified endostatin as disclosed in the present invention can be used in conjunction with a chemotherapeutic agent. The term "chemotherapy agent", or "chemotherapeutic agent" refers to a chemical, or a biological molecule, or compound which can be used in reducing the growth of cancer cells in vitro, or the growth of cancer in a subject such as an animal, or a human. Examples of chemotherapeutic agents include, but are not limited to, cisplatin, vinorelbine, Alimita, ifosfamide, taxanes such as taxol and paclitaxol, topoisomerase I inhibitors (e.g., CPT-11, topotecan, 9-AC, and GG-211), gemcitabine, vinorelbine, oxaliplatin, 5-fluorouracil (5-FU), leucovorin, temodal, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin homologs, and cytoxan. For more information on chemotherapy, refer to Dorr, R. T. and Von Hoff, D. D., eds. (1994) "Cancer Chemotherapy Handbook" 2nd ed. (Appleton and Lange). See also Schiller, et al., N Engl J Med, Vol. 346, No. 2, pp. 92-98 (2002).

Alternatively, the modified endostatin can be used in conjunction with radiation therapy (e.g., gamma radiation or x-ray radiation). Here, the term "radiation therapy" is used interchangeably with the term "radiotherapy". Any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma ray emitting radioisotopes, such as radioactive isotopes of radium, cobalt and other elements may also be administered to expose tissues to radiation.

One aspect of the present invention includes the sequential or concomitant administration of a modified endostatin and a cancer therapy agent such as a chemotherapy agent or a radiation therapy agent. The invention encompasses combinations of the modified endostatin and a cancer therapy agent that are additive or synergistic.

The present invention also provides methods for treating a solid tumor comprising administering to an animal in need thereof, a pharmaceutical composition of the invention and at least one other known cancer therapy. In a specific embodiment, an animal with a solid tumor cancer is administered a pharmaceutical composition of the invention and at least one chemotherapeutic agent.

The present invention includes the sequential or concomitant administration of pharmaceutical composition of the invention, which contains a modified endostatin, and a cancer therapy agent such as a chemotherapy agent. In a specific embodiment, the pharmaceutical composition of the invention is administered prior to (e.g., 1 hour, 2 hours, 3 hours, 4 hours, 5 hours, 6 hours, 12 hours, 1 day, 2 days, 3 days, 4 days, 5 days, 6 days, 7 days, 8 days, 9 days, 10 days, 1 month or several months before) the administration of the anti-cancer agent. In another specific embodiment, the pharmaceutical composition of the invention is administered subsequent to (e.g., 1 hour, 2 hours, 3 hours, 4 hours, 5 hours, 6 hours, 12 hours, 1 day, 2 days, 3 days, 4 days, 5 days, 6 days, 7 days, 8 days, 9 days, 10 days, 1 month or several months after) the administration of a cancer therapy agent. In a specific embodiment, the pharmaceutical composition of the invention is administered concomitantly with an anti-cancer agent.

The present invention includes the pre-set intervals for the administration of the modified endostatin in combination with another cancer therapy agent, such as a chemotherapy agent. For example, in a preferred embodiment of the method, the invention discloses that where the chemotherapy agent is vinorelbine and cisplatin (NP), the vinorelbine can be administered on day 1 and day 5, and the cisplatin can be administered on days 2, 3, and 4, while the modified endostatin can be administered daily from day 1 to day 4. Other frequency of administration and regimen can be utilized depending on the specific chemotherapy agent and the disease indication. For similar reasons, where the cancer therapy agent is a radiotherapy agent, specific administration pattern and regimen can be devised and adapted accordingly. Other cancer therapy agents which may be administered in combination with the modified endostatin include: cisplatin and paclitaxel therapy, cisplatin and gemcitabine therapy, docetaxel and cisplatin, and paclitaxel and carboplatin therapy.

The invention also encompasses combinations of cancer therapy agents and the modified endostatin that have different sites of action. Such a combination provides an improved therapy based on the dual action of these therapeutics whether the combination is synergistic or additive. Thus, the novel combinational therapy of the present invention yields improved efficacy over either agent used as a single-agent therapy.

In one embodiment, an animal, in particular, a human patient, having a solid cancer is administered a pharmaceutical composition of the invention, which contains a modified endostatin, and treated with radiation therapy (e.g., gamma radiation or x-ray radiation). In a specific embodiment, the invention provides a method to treat or prevent cancer that has shown to be refractory to radiation therapy. The pharmaceutical composition may be administered concurrently with radiation therapy. Alternatively, radiation therapy may be administered subsequent to administration of a pharmaceutical composition of the invention, preferably at least an hour, five hours, 12 hours, a day, a week, a month, more preferably several months (e.g., up to three months), subsequent to administration of a pharmaceutical composition.

The radiation therapy administered prior to, concurrently with, or subsequent to the administration of the pharmaceutical composition of the present invention can be administered by any method known in the art. Any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma ray emitting radioisotopes, such as radioactive isotopes of radium, cobalt and other elements may also be administered to expose tissues to radiation.

In addition, the invention also provides methods of treatment of cancer with a pharmaceutical composition as an alternative to radiation therapy where the radiation therapy has proven or may prove too toxic, i.e., results in unacceptable or unbearable side effects, for the subject being treated.

The pharmaceutical compositions of the invention are preferably tested in vitro, and then in vivo for the desired therapeutic or prophylactic activity, prior to use in humans. For example, in vitro assays which can be used to determine whether administration of a specific pharmaceutical composition is indicated, include in vitro cell culture assays in which a patient tissue sample is grown in culture, and exposed to or otherwise administered a pharmaceutical composition, and the effect of such composition upon the tissue sample is observed.

Pharmaceutical compositions of the invention can be tested for their ability to reduce tumor formation in animals suffering from cancer. Pharmaceutical compositions of the invention can also be tested for their ability to alleviate of one or more symptoms associated with a solid tumor cancer. Further, pharmaceutical compositions of the invention can be tested for their ability to increase the survival period of patients suffering from a solid tumor cancer. Techniques known to those of skill in the art can be used to analyze the function of the pharmaceutical compositions of the invention in animals.

Pharmaceutical compositions of the invention for use in therapy can be tested in suitable animal model systems prior to testing in humans, including but not limited to rats, mice, chicken, cows, monkeys, pigs, dogs, rabbits, etc. For in vivo testing, prior to administration to humans, any animal model system known in the art may be used.

According to the present invention, the modified endostatin is advantageously used in methods to inhibit the growth of a tumor, reduce the volume of a tumor, or prevent the spread of tumor cells in an animal, including a human patient, having a solid tumor. In a preferred embodiment, the animal is a mammal. In a highly preferred embodiment, the animal is a human.

Solid tumors include, but are not limited to, sarcomas, carcinomas and other solid tumor cancers, including, but not limited to germ line tumors, tumors of the central nervous system, breast cancer, prostate cancer, cervical cancer, uterine cancer, lung cancer, ovarian cancer, testicular cancer, thyroid cancer, astrocytoma, glioma, pancreatic cancer, stomach cancer, liver cancer, colon cancer, melanoma, renal cancer, bladder cancer, and mesothelioma. The subject is preferably an animal, including but not limited to animals such as cows, pigs, chickens, dogs, cats, horses, etc., and is preferably a mammal, and most preferably human. As used herein, treatment of a solid tumor, includes but is not limited to, inhibiting tumor growth, inhibiting tumor cell proliferation, reducing tumor volume, or inhibiting the spread of tumor cells to other parts of the body (metastasis).

The present invention provides a pharmaceutical composition comprising a pharmaceutically acceptable carrier and a modified endostatin. In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a suspending agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the pharmaceutical composition of the present invention which will be effective in the treatment or prevention of a solid tumor cancer will depend on the nature of the cancer, and can be determined by standard clinical techniques. In addition, in vitro assays may optionally be employed to help identify optimal dosage ranges. The precise dose to be employed in the formulation will also depend on the route of administration, and the seriousness of the cancer, and should be decided according to the judgment of the practitioner and each patient's circumstances. However, suitable dosage ranges are generally depending upon the particular application of the modified endostatin. Effective doses may be extrapolated from dose-response curves derived from in vitro or animal model test systems.

Various delivery systems are known and can be used to administer a pharmaceutical composition of the present invention. Methods of introduction include but are not limited to intradermal, intramuscular, intraperitoneal, intravenous, subcutaneous, intrathecal, intranasal, epidural, and oral routes. Methods of introduction may also be intra-tumoral (e.g., by direct administration into the area of the tumor).

The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, by injection, by means of a catheter, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

The modified endostatin may be delivered in a controlled release system. In one embodiment, a pump may be used (see Langer, supra; Sefton, CRC Crit. Ref. Biomed. Eng. 14:201 (1987); Buchwald et al., 1980, Surgery 88:507; and Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., 1985, Science 228:190; During et al., 1989, Ann. Neurol. 25:351; and Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, Science 249:1527-1533) and may be used in connection with the administration of the modified endostatin.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The modified endostatin described above can be provided as isolated and substantially purified proteins and protein fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In a preferred embodiment, the pharmaceutical composition comprises endostatin combined with sucrose octasulfate.

Additionally, the modified endostatin may be incorporated into biodegradable polymers allowing for sustained release of the endostatin, the polymers being implanted in the vicinity of where drug delivery is desired, for example, at the site of a tumor or implanted so that the endostatin is slowly released systemically. Osmotic minipumps may also be used to provide controlled delivery of high concentrations of endostatin through cannulae to the site of interest, such as directly into a metastatic growth or into the vascular supply to that tumor. The biodegradable polymers and their use are described, for example, in detail in Brem et al., J. Neurosurg. 74:441-446 (1991), which is hereby incorporated by reference in its entirety.

The dosage of the modified endostatin of the present invention will depend on the disease state or condition being treated and other clinical factors such as weight and condition of the human or animal and the route of administration of the modified endostatin. For treating humans or animals, between approximately 0.5 mg/kilogram to 500 mg/kilogram of the modified endostatin can be administered. A more preferable range is 1 mg/kilogram to 100 mg/kilogram with the most preferable range being from 2 mg/kilogram to 50 mg/kilogram. Depending upon the half-life of the modified endostatin in the particular animal or human, the modified endostatin can be administered between several times per day to once a week. It is to be understood that the present invention has application for both human and veterinary use. The methods of the present invention contemplate single as well as multiple administrations, given either simultaneously or over an extended period of time. Preferred unit dosage formulations are those containing a daily dose or unit, daily sub-dose, as herein above recited, or an appropriate fraction thereof, of the administered ingredient. It should be understood that in addition to the ingredients particularly mentioned above, the formulations of the present invention may further include other agents conventional in the art having regard to the type of formulation in question.

The dosage administered will be a therapeutically effective amount of the modified endostatin sufficient to result in amelioration of symptoms of the angiogenesis-related disease and will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired.

Toxicity and therapeutic efficacy of such modified endostatin can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Those modified endostatin molecules which exhibit large therapeutic indices are preferred.

The data obtained from the cell culture assays and animal studies can be used in formulating a range of dosage for use in humans and cats. The dosage of such modified endostatin lies preferably within a range of circulating concentrations that include the $ED_{50}$ with little or no toxicity. The dosage may vary within this range depending upon the dosage form employed and the route of administration utilized. For any modified endostatin used in the method of the invention, the therapeutically effective dose can be estimated initially from cell culture assays. A dose may be formulated in animal models to achieve a circulating plasma concentration range that includes the $IC_{50}$ (i.e., the concentration of the test molecule which achieves a half-maximal inhibition of symptoms) as determined in cell culture. Such information can be used to more accurately determine useful doses in humans and cats. Levels in plasma may be measured, for example, by high performance liquid chromatography.

The modified endostatin can be used in formulations which include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The endostatin formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Pharmaceutical compositions having a modified endostatin for use in accordance with the present invention may be formulated in conventional manner using one or more physiologically acceptable carriers or excipients. Thus, the modified endostatin and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable carriers such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active ingredient, in this case, the modified endostatin. For buccal administration the compositions may take the form of tablets or lozenges formulated in conventional manner.

For administration by inhalation, the modified endostatin for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insulator may be formulated containing a powder mix of the modified endostatin and a suitable powder base such as lactose or starch.

The modified endostatin may be formulated for parenteral administration by injection, e.g., by bolus injection or continuous infusion. The resulting formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the modified endostatin may be in powder form for constitution with a suitable vehicle, e.g., sterile pyrogen-free water, before use. In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The modified endostatin may also be formulated in rectal compositions such as suppositories or retention enemas, e.g., containing conventional suppository bases such as cocoa butter or other glycerides.

In addition to the formulations described previously, the modified endostatin may also be formulated as a depot preparation. Such long acting formulations may be administered by implantation (for example subcutaneously or intramuscularly) or by intramuscular injection. Thus, for example, the modified endostatin may be formulated with suitable polymeric or hydrophobic materials (for example as an emulsion in an acceptable oil) or ion exchange resins, or as sparingly soluble derivatives, for example, as a sparingly soluble salt.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release.

The compositions containing a modified endostatin may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Useful pharmaceutical dosage forms, for administration of the modified endostatin of this invention can include the following applications:

Capsules: Capsules are prepared by filling standard two-piece hard gelatin capsulates each with the desired amount of powdered active ingredient, 175 milligrams of lactose, 24 milligrams of talc and 6 milligrams magnesium stearate. Soft Gelatin Capsules: A mixture of modified endostatin in soybean oil is prepared and injected by means of a positive displacement pump into gelatin to form soft gelatin capsules containing the desired amount of the modified endostatin. The capsules are then washed and dried. Tablets: Tablets are prepared by conventional procedures so that the dosage unit is the desired amount of modified endostatin. 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption. Injectable: A parenteral composition suitable for administration by injection is prepared by stirring 1.5% by weight of active ingredients in 10% by volume propylene glycol and water. The solution is made isotonic with sodium chloride and sterilized. Suspension: An aqueous suspension is prepared for oral administration so that each 5 millimeters contain 100 milligrams of finely divided active ingredient, 200 milligrams of sodium carboxymethyl cellulose, 5 milligrams of sodium benzoate, 1.0 grams of sorbitol solution U.S.P. and 0.025 millimeters of vanillin.

These methods described herein are by no means all-inclusive, and further methods to suit the specific application will be apparent to the ordinary skilled artisan. Moreover, the effective amount of the compositions can be further approximated through analogy to molecules known to exert the desired effect.

The following examples are offered by way of example, and are not intended to limit the scope of the invention in any manner. Further details of the present invention will be apparent from the following Examples and the accompanying drawings which are included by way of illustration, not by way of limitation, of this invention. This application is intended to cover those changes and substitutions which may be made by those skilled in the art without departing from the spirit and the scope of the appended claims.

All publications, patents, and patent applications cited herein are hereby incorporated by reference in their entirety, to the extent they are not inconsistent with the explicit teachings herein.

EXAMPLES

Example 1

Objective: To compare the response rate, median time to progression (TTP), clinical benefit, and safety in patients with advanced non-small cell lung cancer (NSCLC), they were treated with either Rh-endostatin (YH-16) (developed by Medgenn Co. Ltd.) plus vinorelbine and cisplatin (NP), or, placebo plus NP.

Methods: We enrolled 493 patients suffering stage IIIB and IV (NSCLC) (confirmed by histology or cytology), with life expectancy >3 months, and WHO performance status score of 0-2. Patients were entered in a double-blind, placebo-controlled, prospectively randomized trial after stratification, either Arm A: NP plus rh-endostatin (n=326; vinorelbine 25 mg/m$^2$ on day 1 and day 5, cisplatin 30 mg/m$^2$ on days 2 to 4, rh-endostatin 7.5 mg/m$^2$ on days 1 to 14), or Arm B: NP plus placebo (n=167; vinorelbine 25 mg/m$^2$ on day 1 and day 5, cisplatin 30 mg/m$^2$ on days 2 to 4, 0.9% sodium-chloride 3.75 ml on days 1 to 14) every 3 weeks for 2-6 cycles. The number of cycles depended upon the patient's response after the second cycle, for instance, those in the CR, PR, or SD group continue to receive treatment; while those in the PD group would stop treatment. Here, CR=complete response; PR=partial response; SD=stable disease; PD=progressive disease. The response and adverse effects were evaluated by an Independent Experts Evaluation Committee (IEEC) before the results and code were opened.

Results: Of the 486 assessable patients, overall response rates were 35.4% in Arm A and 19.5% in Arm B (P=0.0003). The median TTP were 6.3 months and 3.6 months for Arm A and B, respectively (P<0.001). The clinical benefit rates were 73.3% in Arm A and 64.0% in Arm B (P=0.035). Grade 3/4 neutropenia, anemia, nausea/vomiting were 28.5%, 3.4%, 8.0% respectively in Arm A, as compared with 28.2%, 3.0%, 6.6% in Arm B (P>0.05). There were 2 treatment-related deaths in Arm A and 1 in Arm B (P>0.05).

Conclusions: The addition of rh-endostatin to NP regimen resulted in significant and clinically meaningful improvement in response rate, median time to tumor progression, and clinical benefit rate compared with NP alone in advanced NSCLC patients. Recombinant rh-endostatin in combination with chemotherapy showed a synergistic activity and a favorable toxicity profile in advanced cancer patients.

In 1971, Folkman J suggested that the growth of tumor depends on angiogenesis, which started a new research field. In order to control tumor growth through inhibiting angiogenesis, researchers in many countries have done significant amount of beneficial work over the past 30 years[1, 2].

Endostatin was initially isolated as an endogenic glycoprotein from the cultured media of a murine hemangioendothelioma cell line. It has homology with the carboxy-terminal of collagen XVIII in extra-cellular matrix, and has shown anti-angiogenesis effect[1]. Recent studies have indicated that Endostatin plays an anti-angiogenesis role through its specific effect on neovascular endothelial cells, inhibiting the migration of endothelial cells, and inducing the apoptosis of endothelial cell. In addition, it can regulate the expression of the endothelial cell growth factors that are localized on the surface of tumor cells, and also regulate the protease activity.

Thus, it inhibits neovascular formation and indirectly induces dormancy and growth regression of tumor cells[3, 4].

In the United States, Entremed produced rh-endostatin using Yeast as an expression system, and carried out phase I and phase II clinical trial in September 1999 and October 2002, respectively[5,6]. In China, Yantai Medgenn Biological Engineering Ltd., Co. developed a new type of rh-Endostatin (YH-16) using *E. coli* as an expression system. Cancer Hospital of Chinese Academy of Medical Sciences finished YH-16 phase I clinical trial in August 2001, and came to the conclusion that human body had good tolerance toward YH-16 injection. In March 2002, YH-16 entered into phase II clinical trial. It was preliminarily observed that YH-16 plus NP regimen had positive clinical effect on lung cancer. To further confirm the effect of YH-16 combined with chemotherapy on advanced NSCLC patients, Cancer Hospital of Chinese Academy of Medical Sciences organized 24 general hospitals and specialized hospitals nationwide and completed a randomized, double-blinded, placebo-parallel controlled, multi-centered phase III clinical trial.

Material and Methods

Patient Case Data and Selection: Patient selection criteria were as follows: ages 18~75, pathologically and cytologically confirmed phase III/IV NSCLC patients who were either initially treated, or re-treated patients (including patients who previously received NP regimen and confirmed to be effective but had withdrawn for more than 6 months, and patients who had withdrawn nitrosocarbamide and mitomycin for more than 6 weeks, withdrawn other chemotherapies more than 1 month), Eastern Cooperative Oncology Group (ECOG) performance status (PS) score of 0~2, and had measurable tumor focus. Here, "N" or "NVB" refers to vinorelbine, and "P" or "DDP" refers to Cisplatin. The patients must have no dysfunction of major organs, and their routine blood rest, liver, renal, and cardiac functions were basically normal, and their life expectancy would be more than three months. Moreover, patients must understand present research and can sign the informed consent form.

Exclusion standards are as follows: patients who had allergic history, who were receiving other anti-tumor treatment or had no measurable tumor focus, and whose metastasis focus of central nervous system had not been controlled, and patients who had major organ malfunction or severe cardiac disease including congestive heart failure, uncontrollable arrhythmia, angina which required long term medicine treatment, heart valve disease, myocardial infarction and intractable hypertension. Women who were in pregnancy or in lactation period, or people whose infected wound were incurable, and who had hardly controlled psychiatric history.

Study design: After signing the "informed consent" form, patients who met the selection criteria were entered into the randomized, double-blinded, placebo-parallel controlled, multi-centered phase III clinical trial. The random number table was developed using SAS software. Initial treated patients and re-treated patients were randomly grouped with a ratio of 2:1, and the treatment and control group also were randomly grouped with a ratio of 2:1. Administration regimen: NP plus YH-16 to treatment group and NP plus placebo to the control.

NP Regimen:

NVB: 25 mg/m$^2$, 100 ml normal saline for 30 minutes, i.v., administered on Day 1, and Day 5;

DDP: 30 mg/m$^2$, 500 ml normal saline for 2 hours, i.v., administered on Day 2, 3, 4. The cycle was 21 days.

YH-16: 7.5 mg/m$^2$, 250 ml normal saline for 3-4 hours, i.v., administered from Day 1 to Day 4.

Placebo (0.9% normal saline plus proper amount of human albumin): 3.75 ml. The usage was the same as YH-16.

The patients in treatment group and control had all finished 2-4 periodical treatments. But the therapeutic efficacy would be evaluated after two cycles. After the treatment had been administered for four weeks, the therapeutic efficacy needs to be evaluated again. Members of Independent Experts Evaluation Committee (IEEC) who were unrelated to the trial were invited to evaluate the efficacy collectively. Afterwards, the results were un-blinded.

Endpoints of the study: Primary endpoints included RR, CBR, and TTP. Secondary endpoints included quality of life (QOL), clinical symptom relief rate, safety and toxicity of the drug. Efficacy and toxicity evaluation were based on the standards made by WHO. CBR was defined as the percentage of cases that were completely relieved, partly relieved, and stable in those efficacy were assessable.

Statistical Analysis: All statistical data were analyzed by SAS software. All statistical tests used double tailed test, a P value$\leq$0.05 was considered statistically significant. We used RR, CBR and TTP as Primary endpoints for efficacy evaluation, and compared intra-group results by $X^2$ test, while using the patient's quality of life (QOL) as secondary indices. We then compared efficacy of the two groups using Wilcoxon rank-sum test, using the Log-Rank test to compare TTP, using Logistics regression to perform the multi-factored analysis of RR, and using the Cox ratio-risk modelling to perform the multi-factored analysis of TTP.

Results

Demographics of the selected patients: There were totally 493 phase III/IV NSCLC patients who were randomly entered into the clinical research in 24 hospitals nationwide from April 2003 to June 2004. The safety in all patients could be valuated, and among them, the efficacy in 486 patients could be evaluated. Among the intention-to-treat population, there were 164 cases of NP plus placebo and 322 cases of NP plus YH-16. As shown in Table 1, group distribution was balanced in sex, age, ECOG score, pathological classification, clinical stage, metastasis and treatment period (P>0.05), which indicates that the two groups can be compared.

TABLE 1

Table 1. Assessable patients characteristics (N = 486)

| | Treatment groups | | | |
|---|---|---|---|---|
| | NP plus YH-16 (n = 322) | | NP plus placebo (n = 164) | |
| Characteristic | No. of patients | % | No. of patients | % |
| Age (years) | | | | |
| Median | 57 | | 55 | |
| Range | 18-76 | | 32-76 | |
| Sex | | | | |
| Male | 229 | 71.1 | 117 | 71.3 |
| Female | 93 | 28.9 | 47 | 28.7 |
| ECOG performance status | | | | |
| 0 | 65 | 20.1 | 31 | 18.9 |
| 1 | 205 | 63.7 | 95 | 57.9 |

TABLE 1-continued

Table 1. Assessable patients characteristics (N = 486)

| Characteristic | Treatment groups | | | |
|---|---|---|---|---|
| | NP plus YH-16 (n = 322) | | NP plus placebo (n = 164) | |
| | No. of patients | % | No. of patients | % |
| 2 | 52 | 16.1 | 38 | 23.2 |
| Histological subtype of tumor | | | | |
| Squamous | 129 | 40.1 | 55 | 33.5 |
| Adenocarcinoma | 165 | 51.2 | 98 | 59.8 |
| Other | 28 | 8.7 | 11 | 6.7 |
| Disease stage | | | | |
| IIIA | 51 | 15.8 | 30 | 18.3 |
| IIIB | 86 | 36.7 | 45 | 27.4 |
| IV | 185 | 57.5 | 89 | 54.3 |
| No. of metastases | | | | |
| 0 | 35 | 10.9 | 20 | 12.2 |
| 1 | 150 | 46.6 | 81 | 49.4 |
| 2 | 92 | 28.6 | 41 | 25.0 |
| ≧3 | 45 | 14.0 | 22 | 13.4 |
| Prior anticancer therapies | | | | |
| Surgery | 36 | 11.3 | 23 | 14.3 |
| Radiotherapy | 35 | 11.0 | 24 | 15.0 |
| Initial Treated | 230 | 71.4 | 117 | 71.3 |
| Re-treated | 92 | 28.6 | 47 | 28.7 |

Abbreviations:
NP, vinorelbine plus cisplatin;
YH-16, recombinant human endostatin;
ECOG, Eastern Cooperative Oncology Group.

Efficacy evaluation: As confirmed by independent efficacy evaluation committee, there were no cases of complete relieved in the group of NP plus YH-16 and the group of NP plus placebo. Comparison of efficacy of group NP plus YH-16 and group NP plus placebo could be seen in Table 2.

TABLE 2

Table 2. Primary endpoints comparison between the two groups

| Outcome | NP plus YH-16 | NP plus placebo | Statistical value | P value |
|---|---|---|---|---|
| Overall response rate (%) | 35.4 | 19.5 | 15.89 | 0.0003 |
| Initial treated | 40.0 | 23.9 | 16.15 | 0.003 |
| Re-treated | 23.9 | 8.5 | 14.82 | 0.03 |
| Clinical benefit rate (%) | 73.3 | 64.0 | 9.27 | 0.035 |
| Initial Treated | 76.5 | 65.0 | 11.56 | 0.02 |
| Re-treated | 65.2 | 61.7 | 3.52 | 0.68 |
| Median TTP (months) | 6.3 | 3.6 | 56.37 | 0.0000 |
| Initial Treated | 6.6 | 3.7 | 44.83 | 0.0000 |
| Re-treated | 5.7 | 3.2 | 13.97 | 0.0002 |

Abbreviations:
NP, vinorelbine plus cisplatin;
YH-16, recombinant human endostatin;
TTP, time to progression.

Overall TTP extended 2.6 months (6.3 months and 3.6 months, P=0.0000), overall RR increased 15.9% (35.4% and 19.5% P=0.0003), overall CBR increased 9.3% (73.3% and 64.0% P=0.035). For initial treated patients in group NP plus YH-16 and group NP plus placebo, median TTP was 6.6 months and 3.7 months respectively (P=0.0000), RR was 40.0% and 23.9% respectively (P=0.003), CBR was 76.5% and 65.0% (P=0.02) for re-treated patients in group NP plus YH-16 and group NP plus placebo, median TTP was 5.7 months and 3.2 months respectively (P=0.0002), RR was 23.9% and 8.5% respectively (P=0.03), CBR was 65.2% and 61.7% (P=0.68). Tumor progression curves of intention treated population as well as initial treated and re-treated patients are shown in FIGS. 1, 2 and 3, respectively.

Single factor analysis on factors affecting efficacy: The factors that might affect median TTP (age, sex, PS, number of metastasis focus, pathological classification, clinical stage, previous therapy) were stratified analyzed, and the results showed that median TTP of group NP plus YH-16 and group NP plus placebo had significantly difference in statistics (Table 3).

TABLE 3

Table 3. Comparison of factors influencing the median TTP of the two groups

| | NP plus YH-16 Median TTP (months) | NP plus placebo Median TTP (months) | P value |
|---|---|---|---|
| Overall median TTP | 6.3 | 3.6 | 0.0000 |
| Age (years) | | | |
| <40 | 6.3 | 3.8 | 0.15 |
| 40-60 | 6.0 | 3.5 | 0.0000 |
| >60 | 6.7 | 3.8 | 0.0000 |
| Sex | | | |
| Male | 5.9 | 3.5 | 0.0000 |
| Female | 6.6 | 4.0 | 0.0000 |
| ECOG performance status | | | |
| 0 | 7.1 | 3.2 | 0.0000 |
| 1 | 6.4 | 3.8 | 0.0000 |
| 2 | 4.5 | 2.8 | 0.032 |
| Histological subtype of tumor | | | |
| Squamous | 6.5 | 3.5 | 0.0000 |
| Adenocarcinoma | 6.5 | 3.6 | 0.0000 |
| Other | 5.3 | 5.1 | 0.87 |
| TNM stage | | | |
| IIIA | 7.2 | 4.1 | 0.0000 |
| IIIB | 6.7 | 3.6 | 0.0000 |
| IV | 5.8 | 3.4 | 0.0000 |
| No. of metastases | | | |
| 0 | 7.2 | 4.0 | 0.0051 |
| 1 | 6.5 | 3.6 | 0.0000 |
| 2 | 5.9 | 3.4 | 0.0013 |
| ≧3 | 5.3 | 2.8 | 0.3070 |
| Prior anticancer therapies | | | |
| Initial Treated | 6.6 | 3.7 | 0.0000 |
| Re-treated | 5.7 | 3.2 | 0.0002 |

Abbreviations:
NP, vinorelbine plus cisplatin;
YH-16, recombinant human endostatin;
TTP, time to progression;
ECOG, Eastern Cooperative Oncology Group.

Previous factors that might affect RR were stratified analyzed, and the difference between group NP plus YH-16 and group NP plus placebo was considered statistically significant. (Table 4).

TABLE 4

Table 4. Stratified analysis of efficacy of the two groups

|  | NP plus YH-16 | | NP plus placebo | | |
| --- | --- | --- | --- | --- | --- |
|  | No. of patients | % | No. of patients | % | P value |
| Overall response rate | 114 | 35.4 | 32 | 19.5 | 0.0003 |
| Age (years) | | | | | |
| <40 | 9 | 32.0 | 3 | 27.3 | 0.77 |
| 40-60 | 66 | 40.2 | 18 | 20.5 | 0.002 |
| >60 | 39 | 30.0 | 11 | 17.0 | 0.049 |
| Sex | | | | | |
| Male | | 32.3 | | 16.2 | 0.001 |
| Female | 40 | 43.0 | 13 | 27.7 | 0.08 |
| ECOG performance status | | | | | |
| 0 | | 49.2 | | 16.1 | 0.002 |
| 1 | 70 | 34.2 | 22 | 23.2 | 0.055 |
| 2 | 12 | 23.1 | 5 | 13.2 | 0.23 |
| Histological subtype of tumor | | | | | |
| Squamous | 49 | 38.0 | 10 | 18.2 | 0.009 |
| Adenocarcinoma | 54 | 32.7 | 17 | 17.4 | 0.007 |
| Other | 11 | 39.3 | 5 | 45.5 | 0.72 |
| TNM stage | | | | | |
| IIIA | 17 | 33.3 | 5 | 16.7 | 0.11 |
| IIIB | 29 | 33.7 | 10 | 22.2 | 0.17 |
| IV | 68 | 36.8 | 17 | 19.1 | 0.003 |
| No. of metastases | | | | | |
| 0 | 11 | 31.4 | 4 | 20.0 | 0.4372 |
| 1 | 51 | 34.0 | 18 | 22.2 | 0.0021 |
| 2 | 39 | 42.4 | 6 | 14.6 | 0.0388 |
| ≧3 | 13 | 28.9 | 4 | 18.2 | 0.7145 |
| Prior anticancer therapies | | | | | |
| Initial Treated | 92 | 40.0 | 28 | 23.9 | 0.003 |
| Re-treated | 22 | 23.9 | 4 | 8.5 | 0.034 |

Abbreviation:
NP, vinorelbine plus cisplatin;
YH-16, recombinant human endostatin;
ECOG, Eastern Cooperative Oncology Group.

Groups were analyzed in stratification about the factors affecting CBR, and results showed that CBR of the initial treated patient were 76.5% and 65.0% respectively; patients whose PS score was 0 were 84.6% and 54.8% (P=0.002), the difference between group NP plus YH-16 and group NP plus placebo was considered statistically significant.

Multi-factor analysis on factors affecting efficacy: We analyzed the factors that might affect RR by logistic regression analysis. Related factor that affected efficacy included treatment groups, sex, previous treatment, body status score, body mass indices (Table 5).

TABLE 5

Table 5. Logistic regression analyses of multiple factors affecting efficacy

|  | P value | Risk ratio | 95% confidence interval |
| --- | --- | --- | --- |
| Treatment group | 0.0006 | 0.44 | 0.28-0.71 |
| Age | 0.18 | 0.99 | 0.97-1.0 |
| Sex | 0.018 | 1.73 | 1.01-2.71 |
| Body mass index | 0.025 | 0.92 | 0.86-0.99 |
| PS of ECOG | 0.012 | 0.64 | 0.45-0.91 |
| Base disease or complications | 0.25 | 0.70 | 0.39-1.28 |
| Course of diseases | 0.59 | 0.99 | 0.97-1.02 |
| Histology | | | |
| TNM stage | 0.69 | 1.00 | 0.51-1.95 |
| No. of metastases | 0.68 | 0.86 | 0.41-1.78 |
| Initial treated or Re-treated | 0.0032 | 0.43 | 0.24-0.75 |

We analyzed the factors that might affect median TTP by multi-factor Cox regression analysis, and only the treatment grouping was the factor that had statistical significance.

Secondary Endpoints: Scores on Quality of Life of 486 patients were analyzed and tabulated together. When compared with baseline, it shows that treatment group and control group had no significant differences in appetite, sleep, pain, tiredness, and clinical symptoms. QOL of two groups and the control were all increased after treatment when compared with pre-treatment. When the treatment ended, QOL score of treatment group increased than that of control (P=0.0155), which was considered statistically significant. After treatment, clinical symptom relief rate (including cough, expectoration, hemoptysis, chest pain) of treatment group was a little higher than that of control, but it had no statistical difference (P>0.05).

Safety and adverse effects: 493 assessable patients with adverse effects received treatment of 1075 cycles, and the number of cycles that patients received was 716 and 359 respectively in group NP plus YH-16 and group NP plus placebo. In the group of NP plus YH-16, average dose patients received was 230 mg/m$^2$ (7.5 mg/m$^2$). The median time that patients had received treatment was 48 days and 43 days, respectively, in the group of NP plus YH-16 and the group of NP plus placebo. There were five patients who died of severe adverse effect, among which, three patients came from group NP plus YH-16 (3/326), while the cause of death were intense abdominal pain and serious infection due to bone marrow depression; and there were 2 patients died in group NP plus placebo (2/167), while they died of serious infection and respiratory function failure. The incidence of serious adverse effect was 0.92% and 1.20% respectively in treatment group and control, but had no statistic difference (P=1.00). The incidence of other adverse effect related to treatment (including Edema of lower extremity, skin eruption, angina, arrhythmia, abnormal ECG) was 5.83% and 4.19% respectively in treatment group and control, but had no statistic difference between the two groups (P=0.53). Results on adverse effects occurred during treatment can be seen in Table 6.

TABLE 6

Table 6. Comparison of adverse effects of two groups (N = 493)

| | NP plus YH-16 | | | | NP plus placebo | | | |
|---|---|---|---|---|---|---|---|---|
| | Total toxic effects | | Grade 3/4 | | Total toxic effects | | Grade 3/4 | |
| | No. of Patients | % | No. of Patient | % | No. of Patient | % | No. of Patient | % |
| Neutropenia | 171 | 52.4 | 93 | 28.5 | 85 | 50.9 | 47 | 8.2 |
| Anemia | 105 | 32.2 | 11 | 3.4 | 47 | 28.1 | 5 | 3.0 |
| Thrombocytopenia | 51 | 15.6 | 7 | 2.1 | 25 | 15.0 | 3 | 1.8 |
| Hemorrhage | 2 | 0.6 | 0 | 0 | 1 | 0.6 | 0 | 0 |
| Nausea/vomiting | 165 | 50.6 | 26 | 8.0 | 90 | 53.9 | 11 | 6.6 |
| Catarrh | 3 | 0.9 | 1 | 0.3 | 0 | 0 | 0 | 0 |
| Diarrhea | 12 | 3.7 | 1 | 0.3 | 8 | 4.8 | 2 | 1.2 |
| Constipation | 55 | 16.9 | 1 | 0.3 | 36 | 21.6 | 2 | 1.2 |
| Aminotransferase | 22 | 6.8 | 2 | 0.6 | 8 | 4.8 | 0 | 0 |
| Total Bilirubin | 6 | 1.8 | 1 | 0.3 | 1 | 0.6 | 0 | 0 |
| Blood creatinine | 0 | 0 | 0 | 0 | 0 | 0 | 0 | 0 |
| Fever | 6 | 1.8 | 0 | 0 | 1 | 0.6 | 0 | 0 |
| Rash | 2 | 0.6 | 1 | 0.3 | 2 | 1.2 | 1 | 0.6 |
| Fatigue | 104 | 31.9 | 12 | 3.7 | 61 | 36.5 | 3 | 1.8 |
| Pain | 38 | 11.7 | 2 | 0.6 | 18 | 10.8 | 4 | 2.4 |
| Allergy | 3 | 0.9 | 1 | 0.3 | 0 | 0 | 0 | 0 |
| Peripheral neurotoxity | 3 | 0.9 | 0 | 0 | 5 | 3.0 | 1 | 0.6 |
| Alopecia | 39 | 12.0 | 0 | 0 | 23 | 13.8 | 2 | 1.2 |
| Arrhythmia | 21 | 6.4 | 1 | 0.3 | 6 | 3.6 | 0 | 0 |

Abbreviation:
NP, vinorelbine plus cisplatin;
YH-16, recombinant human endostatin.

Discussions: Lung cancer is one of common tumors which seriously threaten people's health at present[8]. Advanced NSCLC chemotherapy effect has not been satisfactory, even though new medicine (gemcitabine, paclitaxel, NVB) and platinum combination formed the third generation of chemotherapy regimen, and its efficacy improved to some degree, but the survival benefit of patient was still limited[9, 10]. So, clinical oncologists are still looking for new treatment means and methods in order to improve efficacy persistently. In recent years, due to the finding that there is an increase of the quantities of endothelial cells in peripheral blood, and the amount of endostatin and VEGF in tumor patients, anti-angiogenesis treatment has been discovered to be one important research field in treating tumor invasion and metastasis[11, 12]. More and more information suggested that the combination of anti-angiogenesis and chemotherapy may improve efficacy and survival benefits. Encouragingly, anti-VEGF antibody bevacizumab (Avastin) combined with chemotherapy was used to treat 813 cases of first time large intestine cancer patients, the results favorably compared to singular chemotherapy, with improved median life expectancy, median TTP, median relief and total efficient rate, and the toxicity related to treatment was controllable[13]. The study in China showed, rh-Endostatin can bind to Nucleolin found in proliferating endothelial cells, and thus effectively suppressed the tumor growth, at the same time showing low toxicity[14].

Clinical efficacy analysis: A randomized, double-blind, placebo-parallel controlled Phase III clinical study was carried out in 493 Phase III/IV NSCLC patients who were treated with NP plus YH-16 and NP plus placebo. Of the 486 assessable, intention-to-treat patients, the total RR of NP plus YH-16 and NP were 35.4% and 19.5% respectively (P=0.0003); the total CBR were 73.3% and 64.0% respectively (P=0.035); the total median TTP were 6.3 months and 3.6 months respectively (P=0.000).

Le Chevalier T et al[15] reported NP regimen resulted in more significantly survival benefits than VDS plus NP in treating advanced NSCLC patients, so established NP regimen as advanced NSCLC standard treatment regimen. SWOG (Southwest Oncology Group) conducted Phase III randomized study and showed[16] that efficacy of the NP regimen in treating advanced NSCLC was 26%, and the non-progression survival time was 4 months. In China, Sun, Y et al conducted Phase III randomized study and reported[17,18] that the efficacy of the NP regimen in treating advanced NSCLC was 42.0%-47.6%, median relief time was 3.3 months.

In the present study, efficacy of the NP regimen was similar to those observed in the randomized study result overseas, and the total efficacy were 19.5% and 26% respectively, median TTP were 3.6 months and 4.0 months respectively. Our efficacy of the NP regimen was lower than domestic other reports, but median TTP were similar, were 3.6 months and 3.3 months respectively. It may be related to the double-blinded, placebo control, multi-centered Phase III clinical study, and conducted strict efficiency confirmation. NP combined with YH-16, the total RR and median TTP were superior significantly to NP plus placebo group. It was showed that NP combined with YH-16 could improve advanced NSCLC patients' RR and lengthen median TTP.

As a first-line treatment for patients who were treated initially, the curative rate of NP plus YH-16 and NP placebo were 40.0% and 23.9% respectively (P=0.003); clinical beneficial rate were 76.5% and 65.0% respectively (P=0.0023); median TTP were 6.6 months and 3.7 months (P=0.0000).

In the TAX326 study of which docetaxel combined with platinum compound and NP regimen used as first-line treatment for advanced NSCLC, the effective rate of NP regimen was 24.5%, median tumor time to progression was 3.1 months[19]. We observed the effective rate of NP regimen was 23.9% and close to TAX326 reported the result of NP regimen. The effective rate of YH-16 combined with NP improved 16% more than NP regimen, and median TTP also lengthened 2.9 months, although we still couldn't observe median life expectancy and 1-year survival rate. The current data have shown that, for YH-16 plus NP as the first-line treatment for advanced NSCLC, the RR and median TTP are superior to NP regimen.

The world famous ECOG1594 study showed that, for the third generation chemotherapy regimen (paclitaxel plus NP, paclitaxel plus CBP, gemcitabine plus DDP, docetaxel plus DDP) used as the first-line treatment, the total effective rate was 19%, the total median TTP was 3.6 months. Noticeably, ECOG1594 was a large-scale Phase III randomized study, and 1207 patients participated in the study. It represented current chemotherapy status of advanced NSCLC[20]. In our study, overall effective determinant were confirmed by independent expert committee, we observed RR and median TTP of NP regimen were similar to that of the currently used the third generation chemotherapy regimen. In our study, for NP plus YH-16 used as the first-line treatment, the RR was significantly improved when compared with NP plus placebo control group (40.0% vs. 23.9%, P=0.003), the median TTP was lengthened significantly (6.6 months vs 3.7 months, P=0.0000), the efficacy of YH-16 plus NP regimen in treating advanced NSCLC may be superior to the current third generation chemotherapy regimen, however, still need to further study to validate.

Currently, docetaxel or Alimita is the second-line standard treatment of NSCLC, and the effective rate was about 10%, the median TTP was around 6 months, 1 year survival rate was 20%[21]. Single drug used in the second-line treatment also included ifosfamide, gemcitabine, NVB et al. but efficacy was all lower than 10%[22,23]. In this study, the RR of the second-line treatment in which NP regimen was only used, was similar to the result of the current standard second-line treatment. The selected patients who were treated again previously weren't treated with NP or treated with NP regimen and obtained efficiency, and stopped taking medicine over 6 months. Compared with NP, the RR of NP plus YH-16 was improved 15.4% (23.9% vs. 8.5%, P=0.034), the median TTP was also lengthened 2.5 months (5.7 months vs 3.2 months, P=0.0002), which showed YH-16 plus NP had synergistic action in treating patients who were treated again, its efficacy was superior to NP. YH-16 combined with chemotherapy may change the status of the current NSCLC second-line treatment in which single medicine is used.

The treatment aim of advanced NSCLC was to relieve symptom, and lengthen life expectancy and improve survival quality[24]. In this study, after treatment, comparing NP plus YH-16 with NP plus placebo control group, the QOL grade was significantly increased (P=0.0155).

Stratification and multi-factor analysis on factors affected efficacy: During the stratification analysis on RR, we noticed the patients whose PS grades were 2, compared treatment group with control group, but we observed the median TTP of these patients was significantly difference (4.5 months vs 2.8 months, P=0.032). Although many large-scale randomized studies showed regimen containing platinum mainly benefited patients whose PS were 0 or 1 from the treatment[25,26], however, we observed NP plus YH-16 also brought survival benefit to patients whose PS were 2.

At present time, combination treatment of the two medicines has been the standard treatment mode for patient with good functional status. However, for the older advanced NSCLC patients, the clinical data sustained to use combination treatment were yet limited. Subgroup analysis of the large-scale Phase III clinical randomized trial showed[27,28] the older patients whose functional status were benign also can receive combination treatment the same as the young patients. The stratification analysis showed the patients whose ages were over 60, compared treatment group with control group, the RR were 30.0% and 16.9% respectively (P=0.049), and had marginal statistical significance. The median TTP of treatment group and control group were 6.7 months and 3.8 months, respectively (P=0.0000), and had significantly statistical difference. Our data showed YH-16 plus NP benefited the older patients whose ages were over 60.

It was reported that the factors affecting chemotherapy efficacy mainly included patients' functional status (PS) and disease grade phase. The factors affecting prognosis included weight decrease, sex, LDH level increase, liver or bone transfer[29]. The measurement of peripheral blood angiogenesis inhibitor may be important for grade phase[30] In our Phase III study, multi-factors Logistic regression analysis conducted on factor affecting RR, and it was proved that treatment grouping was the most important effective factor (P=0.0006). The first treatment or re-treatment was the most important factor affecting RR (P=0.0032). In addition, PS, weight index, sex were also more important factors that affected efficacy (its dedicative P value were 0.012, 0.025, 0.018, respectively).

RR and CBR were the near future evaluation standard of the efficacy. The far future evaluation standard of the efficacy was survival benefit. Life expectancy was the goal index of the survival benefit, whose optimal replace index was TTP, because TTP was positive correlation to life expectancy. So we conducted multi-factors Cox regression analysis on factors that affected TTP, which proved YH-16 combined with chemotherapy was the most important factor in affecting TTP.

We conclude from the single-factor analysis and further proved in multi-factor analysis, for advanced NSCLC patients, YH-16 combined with chemotherapy could not only improve RR and median TTP, but was the most significant factor that affected efficacy.

Safety analysis: The study showed that, there had no significant difference of changes of heart rate, breath rate, blood pressure and other life sign between patients in NP combined with YH-16 group and NP plus placebo control group, and the safety was satisfied. During the trial, 5 patients died, but there wasn't statistical difference between two groups. There wasn't also statistical difference of adverse effect related to treatment (included lower limb dropsy, tetter, angina cordis, arrhythmia, cardiogram abnormity). In the course of treatment, there wasn't seriously adverse effect related to YH-16 treatment. We observed in this study that adverse effect over 10% were neutrophil decrease, anemia, haematoblast decrease, nausea/vomit, astriction, lose hair, fatigue, ache, but there wasn't statistical difference between two groups.

Overseas Rh-endostatin phase I clinical trial and our phase I, II clinical trial all found that Rh-endostatin could result in supraventricular tachycardia. During the Phase III clinical trial, we observed arrhythmia incidence in NP plus YH-16 treatment group was a little higher than that in NP group, but there wasn't statistical significance (P=0.391). Whether YH-16 could aggravate arrhythmia adverse effect needs further study.

Conclusions: A randomized, double-blinded, placebo-parallel controlled, multi-centered Phase III clinical study in which YH-16 combined with NP were used to treat advanced NSCLC showed that YH-16 plus NP could significantly improve total RR, CBR, median TTP and QOL. The combination of YH-16 and NP had synergistic action, and didn't significantly increase adverse reaction during chemotherapy; however, it should be carefully administrated for patients suffering from heart disease. YH-16 combined with chemotherapy was a safe, effective treatment regimen for advanced NSCLC, and was also a successful example of the chemotherapy combined with target medicine, and it also had an encouraging clinical application perspective.

Under the present condition, if we can measure the tumor receptor and the level of peripheral endostatin and thus enhance drug targeting, the clinical therapeutic efficacy will be undoubtedly improved accordingly.

Example 2

Follow-up Studies: To follow up on the patients of the clinical trial, we analyzed 475 patients' living status by follow-up till March, 2005, including 312 patients in treatment group of which median follow-up time was 13.1 months (the duration of follow-up was 0.33 months~22.50 months) and 163 patients in control group of which follow-up time was 9.6 months (the duration of follow-up was 0.46 month~20.72 months). In treatment group 156 patients died (3 non-tumor patients among them), 151 survived and 5 missed follow-up, while 119 died, 43 survived and 1 missed follow-up in control group.

The flowing is the comparison of living status of the two groups. We refer to Table 7 to compare with the two groups in median life expectancy and one-year survival rate.

TABLE 7

Table 7. Comparison of the median survival rate and one year survival rate

| | Characters | ITT | | | | PP | | | |
|---|---|---|---|---|---|---|---|---|---|
| | | NP + YH-16 | NP | Statistical value | P value | NP + YH-16 | NP | Statistical value | P value |
| Overall | Median survival (months) | 14.87 | 9.90 | 35.32(1) | 0.0000 | 15.86 | 9.90 | 35.32(1) | 0.0000 |
| | 1-year survival (%) | 62.75 | 31.46 | | | 64.68 | 31.86 | | |
| Initial treated | Median survival (months) | 15.16 | 9.77 | 30.60(1) | 0.0000 | 15.86 | 9.77 | 30.60(1) | 0.0000 |
| | 1-year survival (%) | 64.08 | 31.83 | | | 66.40 | 32.10 | | |
| Re-treated | Median survival (months) | 14.67 | 10.00 | 5.54(1) | 0.0186 | 15.69 | 10.00 | 5.54(1) | 0.0186 |
| | 1-year survival (%) | 59.45 | 29.87 | | | 60.26 | 30.55 | | |

Abbreviation:
ITT, intention-to-treat;
PP, Per Protocol.

The median life expectancy of NP plus YH-16 group was 14.87 months, including initial treated and re-treated patients whose median life expectancies were 15.16 months and 14.67 months respectively. The median life expectancy of NP group was 9.9 months whose initial treated and re-treated patients median life expectancies were 9.77 and 10.00 months.

The one-year survival rate of NP plus YH-16 group was 62.75% and NP group was 31.46%. One-year survival rate of the initial treated and re-treated in the former group were 64.08% and 59.45% while 31.83% and 29.87% were in the latter group.

The living status of the two groups had significant difference. P value <0.05 in each comparison by log rank test FIGS. 4, 5 and 6 showed the comparisons of the two groups in the survival Kaplan-Meier Curves.

The multiple factor Cox regression analysis of the survival rate of the two groups was showed in Table 8.

Relief: the dead risk was half less in relieved patients than those non-relieved (RR=0.46, P=0.0000).

Treatment periods: the progressing risk was lower when patients were in the long treatment periods. Extending one period, the risk lessened about 60% in average (RR=0.51, P=0.0000).

The life expectancy was the terminal index to evaluate whether patients could benefit from a certain treatment in life expectancy. It was not only related to body status (body status and tumor clinical stages) of a patient but also to treatments. Our research showed that the patients' life expectancies extended obviously and the patients could benefit in the ultimate if YH-16 combined with chemotherapy, the patients' tumor could be relieved and patients were treated with longer

TABLE 8

Table 8. Multiple factored Cox regression analysis of patient survival (ITT, PP)

| | ITT | | | PP | | |
|---|---|---|---|---|---|---|
| | RR(95% CI) | Wald Chi Square(df) | P value | RR(95% CI) | Wald Chi Square(df) | P value |
| Placebo or YH-16 | 2.07(1.59, 2.69) | 29.7(1) | 0.0000 | 2.05(1.56, 2.68) | 27.4(1) | 0.0000 |
| Age | 0.99(0.98, 1.01) | 0.6(1) | 0.4377 | 0.99(0.98, 1.01) | 0.7(1) | 0.4171 |
| Body mass index | 1.44(1.14, 1.81) | 9.5(1) | 0.0021 | 1.41(1.11, 1.79) | 7.8(1) | 0.0053 |
| MBI | 0.98(0.94, 1.03) | 0.6(1) | 0.4566 | 0.99(0.95, 1.04) | 0.1(1) | 0.8127 |
| Course of diseases (months) | 0.99(0.98, 1.01) | 1.0(1) | 0.3060 | 0.99(0.97, 1.00) | 2.3(1) | 0.1254 |
| Sex | 0.90(0.66, 1.23) | 0.4(1) | 0.5129 | 0.94(0.68, 1.29) | 0.2(1) | 0.6902 |
| Initial treated or Re-treated | 0.76(0.54, 1.06) | 2.6(1) | 0.1089 | 0.77(0.54, 1.10) | 2.1(1) | 0.1474 |
| Disease stage | 1.26(1.04, 1.54) | 5.3(1) | 0.0212 | 1.22(0.99, 1.50) | 3.7(1) | 0.0560 |
| Whether metastases | 1.06(0.68, 1.65) | 0.1(1) | 0.7931 | 1.17(0.74, 1.85) | 0.5(1) | 0.4978 |
| Base disease response | 0.97(0.67, 1.40) | 0.0(1) | 0.8694 | 0.94(0.64, 1.39) | 0.1(1) | 0.7680 |
| Treatment cycle | 0.46(0.32, 0.65) | 19.0(1) | 0.0000 | 0.44(0.31, 0.63) | 20.3(1) | 0.0000 |
| | 0.51(0.40, 0.65) | 29.3(1) | 0.0000 | 0.54(0.42, 0.70) | 22.1(1) | 0.0000 |

Abbreviation:
ITT, intention-to-treat;
PP, Per Protocol;
RR, relative risk;
CI, confidence interval; MBI.
Note:
response = CR + PR We applied multiple factor Cox regression analysis to analyze the factors that maybe affect the patients' life expectancies. The results showed that treatment grouping, body status scores clinical stages, relief and treatment periods were correlation factors to patients' life expectancies.

Treatment grouping: YH-16 group was 2.07 times less than the placebo group (RR=2.07, P=0.0000).

Physical status scores: a patient with better physical status (higher ECOG scores) had longer life expectancy (RR=1.44, P=0.0021).

Clinical stages: a patient in III stage had longer life expectancy than IV stage (RR=1.26, P=0.0212).

periods. Patients could be recommended to apply YH-16 as early as possible in clinic, if they could tolerate, extend the treatment as long as possible.

REFERENCES

1. Folkman J. Role of angiogenesis in tumor growth and metastasis. Semin Oncol, 2002, 29(6 suppl 16): 15-18.

2. Li Shu-ting, Sun Yan, Angiogenesis Inhibitors: Research History, Current Development, and Future Perspective. Progress in Clinical Oncology, 2003, 1: 80-87.

3. Huang X, Wong M K, Zhao Q, et al. Soluble recombinant endostatin purified from *Escherichia coli*: antiangiogenic activity and antitumor effect. Cancer Res, 2001, 61:478-481.

4. Bing Li, Xiaoyu Wu, Hao Zhou, et al, Acid-induced unfolding mechanism of recombinant human endostatin. Biochemistry, 2004, 43:2550-2557.

5. Eder J P Jr, Supko J G, Clark J W, et al. Phase I clinical trial of recombinant human endostatin administered as a short intravenous infusion repeated daily. J Clin Oncol, 2002, 20:3772-3784.

6. Kulke M, Bergsland E, Ryan D P, et al. A phase II, open-label, safety, pharmacokinetic, and efficacy study of recombinant human endostatin in patients with advanced neuroendocrine tumors. Proc ASCO, 2003, 22: 958.

7. Yang Lin, Wang Jin-wan, Tang Zhong-ming, et al. Phase I clinical trial for recombinant human endostatin. Chinese Journal of New Drugs, 2004, 6: 548-553.

8. Sun Y. The Onset of Cancer, Its Early Prevention, Diagnosis, and Treatment. China Medical Tribune, 2004-12-9, 938.

9. Scagliotti G V, De Marinis F, Rinaldi M, et al. Phase III randomized trial comparing three platinum-based doublets in advanced non-small-cell lung cancer. J Clin Oncol, 2002, 20: 4285-91.

10. Gebbia V, Galetta D, Caruso M, et al. Gemcitabine and cisplatin versus vinorelbine versus vinorelbine and cisplatin followed by ifosfamide and gemcitabine in stage IIIB-IV non-small cell lung carcinoma: a prospective randomized phase III trial of the Grouppo Oncologico Meridionale. Lung Cancer, 2003, 39:179-89.

11. Li Hui, Zhang Peng, Ren Xiu-bao et al. Relation of the Amount of Circulating Endothelial Cells in Peripheral Blood and the Serum Level of VEGF in Tumor Patients. Chinese J Cancer Biother, 2003, 10: 194-197.

12. Zhou Q H, Sun Y. Enhance the basis of molecular target therapy and clinical research of national lung cancer. Chinese J Lung Cancer, 2004, 7: 267-269.

13. Hurwitz H, Fehrenbacher L, Novotny W, et al. Bevacizumab plus irinotecan, fluorouracil, and leucovorin for metastatic colorectal cancer. N Engl J Med, 2004, 350(23): 2335-42.

14. Hubing Shi, Yujie Huang, Yongzhang Luo, et al. Shuttle protein nucleolin is a receptor for endostatin signal network. Unpublished data.

15. Le Chevalier T, Brisgand D, Doulliard J Y, et al: Randomized trial of vinorelbine and cisplatin versus vindesine and cisplatin versus vinorelbine alone in advanced non-small-cell lung cancer: Results of a European multicenter trial including 612 patients. J Clin Oncol, 1994, 12:360-367.

16. Wozniak A J, Crowley J J, Balcerzak S P, et al: Randomized trial comparing cisplatin with cisplatin plus vinorelbine in the treatment of advanced non-small-cell lung cancer: A Southwest Oncology Group study. J Clin Oncol, 1998, 16:2459-2465.

17. Sun Yan, Zhang Xiangru, Zhang Heping, et al Vinorelbine in the management of advanced maligncies results of a phase III clinical trial in China. Chinese Journal of New Drugs, 1998, 7: 262-265.

18. Zhang Xiang -ru, Sun Y, Kong Wei-hong, et al. Navelbine plus cisplatin combination therapy in the treatment of advanced non-small cell lung cancer: a report of 42 cases. Chinese J Oncol, 1998, 20: 60-62.

19. Fossella F, Pereira J R, von Pawel J, et al. Randomized, multinational, phase III study of docetaxel plus platinum combinations versus vinorelbine plus cisplatin for advanced non-small-cell lung cancer: the TAX 326 study group. J Clin Oncol, 2003, 21:3016-24.

20. Schiller J H, Harrington D, Belani C P, et al: Comparison of four chemotherapy regimens for advanced non-small cell lung cancer. N Engl J Med, 2002, 346:92-98.

21. Shepherd F. Second-line chemotherapy for non-small-cell lung cancer. Edu Book Am Soc Clin Oncol, 2003, 39: 650-653.

22. Shepherd F, Dancey J, Ramlau R, et al: A prospective randomized trial of docetaxel (Taxotere) versus best supportive care in patients with non-small cell lung cancer previously treated with platinum-based chemotherapy. J Clin Oncol, 2000, 18: 2095-2013.

23. Fossella F V, DeVore R, Kerr R N, et al: Randomized phase III trial of docetaxel versus vinorelbine or ifosfamide in patients with advanced non-small cell lung cancer previously treated with platinum-containing chemotherapy regimens. J Clin Oncol, 2000, 18: 2354-2362.

24. Luo J, Sun Y. Study of cancer patients living quality. Medical Oncology, 2001, 324-340, People's Medical Publishing House.

25. Soria J C, Brisgand D, Le Chevalier T. Do all patients with advanced non-small-cell lung cancer benefit from cisplatin-based combination therapy? Ann Oncol. 2001, 12: 1667-70.

26. Kelly K, Crowley J, Bunn P A Jr. et al. Randomized phase III trial of paclitaxel plus carboplatin verus vinorebine plus cisplatin in the treatment of patients with advanced non-small-cell lung cancer: a Southwest Oncology Group trial. J Clin Oncol, 2001, 19:3210-8.

27. Hennessy B T, Hanrahan E O, Breathnach O S. Chemotherapy options for the elderly patient with advanced non-small-cell lung cancer. Oncologist, 2003, 8: 270-7.

28. Gridelli C. Chemotherapy of non-small cell lung cancer in the elderly. Lung Cancer, 2002, 38 Suppl 3:S67-70.

29. Feld R, Borges M, Giner V, et al. Prognostic factors in non-small cell lung cancer. Lung Cancer, 1994, 11 Suppl 3:S19-23.

30. Wang Ying, Shi Dian-peng, Yu Jin-ming, et al. Serum Endostatin Levels in Patients with Primary Lung Cancer. China J Cancer Prev Treat, 2003, 10: 925-927.

What is claimed is:

1. A method of treating an angiogenesis-related disease of a subject, comprising the step of administering a modified endostatin to the subject in a therapeutically effective amount, in addition to treating the subject with a known therapy suitable for treating said angiogenesis-related disease, wherein the modified endostatin is an endostatin molecule having at its N terminal an additional amino acid sequence as set forth in SEQ ID NO:1 or SEQ ID NO:2.

2. The method of claim 1, wherein said subject is a human.

3. The method of claim 1 wherein said angiogenesis-related disease is cancer.

4. The method of claim 1, wherein the modified endostatin is administered to the subject together with a pharmaceutically acceptable carrier.

5. The method of claim 1, wherein the known therapy is a cancer therapy.

6. The method of claim 5 wherein the cancer therapy is a chemotherapy.

7. The method of claim 6, wherein the chemotherapy is selected from vinorelbine therapy, cisplatin therapy, and combinations thereof.

* * * * *

```
                            SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 1

Met Gly Gly Ser His His His His His
 1               5

<210> SEQ ID NO 2
<211> LENGTH: 15
<212> TYPE: PRT
<213> ORGANISM: Artificial Sequence
<220> FEATURE:
<223> OTHER INFORMATION: Plus N-terminal 9 amino acid sequence of native
      rhEndostatin

<400> SEQUENCE: 2

Met Gly Gly Ser His His His His His Ser His Arg Asp Phe
 1               5                  10                  15
```